(12) United States Patent
Stefan et al.

(10) Patent No.: US 11,141,235 B2
(45) Date of Patent: Oct. 12, 2021

(54) AUTOCLAVABLE HANDLE

(71) Applicant: Karl Storz SE & Co. KG, Tuttlingen (DE)

(72) Inventors: Jochen Stefan, Tuttlingen (DE); Claus Kramer, Tuttlingen (DE); Sven Grüner, Tuttlingen (DE); Chunman Fan, Tuttlingen (DE); Kay Behrendt, Tuttlingen (DE); Andreas Bayer, Tuttlingen (DE)

(73) Assignee: Karl Storz SE & Co. KG, Tuttlingen (DE)

(*) Notice: Subject to any disclaimer, the term of this patent is extended or adjusted under 35 U.S.C. 154(b) by 299 days.

(21) Appl. No.: 16/422,039

(22) Filed: May 24, 2019

(65) Prior Publication Data
US 2019/0357991 A1 Nov. 28, 2019

(30) Foreign Application Priority Data

May 28, 2018 (DE) ...................... 10 2018 004 244.9

(51) Int. Cl.
*A61B 90/00* (2016.01)
*A61B 34/30* (2016.01)
*A61B 46/10* (2016.01)
*A61B 34/00* (2016.01)
*A61B 17/00* (2006.01)

(52) U.S. Cl.
CPC .............. *A61B 90/08* (2016.02); *A61B 34/30* (2016.02); *A61B 46/10* (2016.02); *A61B 34/74* (2016.02); *A61B 2017/0023* (2013.01); *A61B 2017/0042* (2013.01); *A61B 2017/0046* (2013.01); *A61B 2017/00367* (2013.01); *A61B 2090/0813* (2016.02)

(58) Field of Classification Search
CPC combination set(s) only.
See application file for complete search history.

(56) References Cited

U.S. PATENT DOCUMENTS

| | | |
|---|---|---|
| 5,712,543 A | 1/1998 | Sjostrom |
| 6,059,806 A | 5/2000 | Hoegerle |
| 6,821,120 B2 | 11/2004 | Suzuki et al. |
| 9,566,121 B2 | 2/2017 | Staunton et al. |
| 2003/0214816 A1 | 11/2003 | Barlian et al. |
| 2006/0100485 A1 | 5/2006 | Arai et al. |

(Continued)

FOREIGN PATENT DOCUMENTS

| | | |
|---|---|---|
| DE | 102004041871 A1 | 3/2006 |
| DE | 202006018987 U1 | 3/2007 |

(Continued)

*Primary Examiner* — Scott Luan
(74) *Attorney, Agent, or Firm* — McGlew and Tuttle, P.C.

(57) ABSTRACT

An autoclavable handle (5) includes a handle housing (9) and with at least one switch element (11) mounted to the handle housing (9). The autoclavable handle (5) is permanently resistant to the effects of machine cleaning and of steam sterilization. The at least one switch element (11) is resiliently pressable into the handle housing (9). The switch element (11) is mounted in the handle housing (9) via at least one web (16) arranged on an underside of the switch element (11). The switch element (11) is sealed off from the handle housing (9) via a circumferential sealing element (12).

20 Claims, 12 Drawing Sheets

(56) References Cited

U.S. PATENT DOCUMENTS

| | | | |
|---|---|---|---|
| 2010/0069940 A1* | 3/2010 | Miller | A61B 17/320068 |
| | | | 606/169 |
| 2015/0202376 A1 | 7/2015 | Haupt | |
| 2015/0223897 A1* | 8/2015 | Kostrzewski | A61B 17/1655 |
| | | | 606/130 |
| 2016/0310134 A1 | 10/2016 | Contini et al. | |
| 2019/0290308 A1* | 9/2019 | Worthington | A61B 17/07207 |

FOREIGN PATENT DOCUMENTS

| | | |
|---|---|---|
| DE | 202009017971 U1 | 12/2010 |
| DE | 102004041871 B4 | 1/2014 |
| EP | 2641550 A2 | 9/2013 |
| EP | 0 834 891 A2 | 4/2018 |

* cited by examiner

AUTOCLAVABLE HANDLE

CROSS REFERENCE TO RELATED APPLICATIONS

This application claims the benefit of priority under 35 U.S.C. § 119 of German Application 10 2018 004 244.9, filed May 28, 2018, the entire contents of which are incorporated herein by reference.

TECHNICAL FIELD

The invention relates to an autoclavable handle with a handle housing and with at least one switch element mounted in the handle housing.

TECHNICAL BACKGROUND

Handles with switch elements, for example with electromechanical buttons, are known as device-bound switching facilities or also as remote controls in a wide variety of embodiments from the private sphere and professional sphere. In medical technology, these handles with the electrical switch elements are an important aid in the interface between the user and the attached device. In operating theaters, these handles which can be used in the sterile region serve to control devices arranged in a non-sterile region or devices which are arranged in the sterile region, for example holding arms or also surgical robots which, since they are not autoclavable as a whole, are covered under sterile drapes and hoods during the operation.

If an operating handle is not intended to be used as a disposable article, it has to be sterilized after each use. The customary form of sterilization is by autoclaving in an autoclave.

In autoclaving, also known as steam sterilization, the fractionated vacuum method is generally used in practice. In this method, a vacuum is generated in the autoclave in the venting phase. Steam is then let into the sterilizing chamber of the autoclave and heated in the sterilization phase to 134° C., and the devices to be sterilized, which are situated in the autoclave, are sterilized at a pressure of 3 bar for a period of at least 5 minutes. In the final drying phase, the steam is let off and, with a new vacuum established, the material to be sterilized is dried. These aforementioned method steps of autoclaving are generally repeated several times.

For the devices that are to be sterilized, this autoclaving process described above places an extraordinary strain on the material and on the seals and, in the case of the handles, also on the electronics.

Handles with electrical switch elements are known in practice which have to be opened and dismantled for sterilization. On account of the joins that are present, these dismantlable handles have the disadvantage that contaminants and moisture can get into the handle during operation. Moreover, the dismantling and subsequent reassembly of the handles takes up a great deal of time and is thus also associated with high operating costs.

DE 10 2004 041 871 B4 discloses an autoclavable remote control unit and a method for producing same. In this known remote control unit, the circuit board provided with the electrical switch elements is encapsulated with silicone in a first work step, such that only the switches or buttons protrude from the silicone potting composition of the base part. In a second work step, the switches or buttons are sealed off via a cover which is made of an autoclavable material and which is connected, for example adhesively bonded, to the silicone potting composition of the base part.

Although the silicone encapsulation of the circuit board fitted with the electrical switch elements permits very good sealing of this base part, this known autoclavable remote control unit also has a join, namely the join between the silicone-embedded base part and the cover. This adhesively bonded join poses two potential problems, firstly as regards the correct and complete formation of the adhesive bond across the whole surface and, secondly, as regards the ageing of the adhesive seam, particularly in the course of the repeated autoclaving.

SUMMARY

Proceeding from this, the object of the invention is to make available an autoclavable handle which is permanently resistant to the effects of machine cleaning and of steam sterilization.

According to the invention, this object is achieved by the fact that the at least one switch element can be pressed resiliently into the handle housing, wherein the switch element is mounted in the handle housing via at least one web arranged on the underside of the switch element, and the switch element is sealed off from the handle housing via a circumferential sealing element.

Through the use of the switch element which can be pressed resiliently into the handle housing, with the circumferential sealing element made of an autoclavable material that sealingly bridges the gap between the movable switch element and the rigid handle housing, a handle is made available which, while being simple and safe to use, does not require any joins in the housing and therefore ensures reliable cleaning in the autoclave.

In a practical embodiment of the invention, it is proposed that the at least one switch element is arranged in a trough-shaped depression of the handle housing, wherein an opening for passage of the at least one web is formed in the depression. The trough-shaped depression for receiving the switch element that can be pressed in can be easily sealed off via the circumferential sealing element that bridges the gap between the movable switch element and the rigid handle housing.

According to a preferred embodiment of the invention, it is proposed that an oblong hole is formed in the at least one web and runs in the longitudinal direction of the web, and the web is mounted in the handle housing via an axle passing through the oblong hole, wherein a spring element is mounted on the switch element in such a way that the spring element presses the switch element outward from the handle housing, such that a working path of the switch element derives from the length of the oblong hole. This type of mounting of the at least one switch element on the one hand ensures a secure and captive bearing of the switch element in the handle housing and on the other hand guarantees at the same time a defined work stroke for the switch element that can be pressed into the handle housing.

In order to allow the switch elements to be pressed resiliently into the handle housing, it is proposed according to the invention that the spring element bears with one end on the underside of the switch element and is supported with the other end on the bottom of the trough-shaped depression of the handle housing. This arrangement of the spring element, with the spring element advantageously arranged in the center of the respective switch element, permits simple assembly and smooth operation of the respective switch element.

In a preferred embodiment according to the invention for forming the switch elements, the at least one switch element is mounted in the handle housing via two webs spaced apart from each other, wherein both webs are mounted on a common axle in the handle housing and, for each web, a separate opening is formed in the trough-shaped depression of the handle housing. The use of two webs spaced apart from each other, with the spring element arranged between the two webs, on the one hand stabilizes the mounting of the switch element on the spring element and on the other hand makes it possible that the switch element can also be actuated by a tilting motion.

To form the handle according to the invention, it is furthermore proposed that the handle housing has a plurality of switch elements mounted in each case in an associated trough-shaped depression of the handle housing, wherein a separate opening is formed in the trough-shaped depression for each web, and the webs of all of the switch elements are mounted on a common axle in the handle housing. The use of a plurality of switch elements in a handle housing can either permit a plurality of switching functions with one handle or can serve to increase the operating safety by the fact that a switching signal is generated only when two or more switch elements are actuated simultaneously.

In order to ensure a reliable seal between, on the one hand, the handle housing and, on the other hand, the switching element that can be pressed in, the invention proposes that the respective circumferential sealing element, via which each switch element is sealed off from the handle housing, is mounted with clamping engagement both on the handle housing and on the respective switch element. Mounting the sealing element with clamping engagement on both sides guarantees a secure and positionally fixed hold of the sealing element even when the associated switch element is actuated.

According to a practical embodiment for forming the sealing element, the invention proposes that each sealing element has two bead-shaped clamping regions which are spaced radially apart from each other and are connected to each other via an elastic connecting web. The elastic connecting web guarantees the resilient pressing of the switch element into the handle housing.

According to the invention, each switch element is advantageously composed of an upper grip plate and a lower screw plate, wherein the circumferential sealing element is secured with clamping engagement in a sealing seat between the grip plate and the screw plate. The use of the two part structure with the lower screw plate has the advantage that the sealing element can be easily secured with clamping engagement on the respective switch element and all of the necessary screw connections are arranged on the underside of the switch element, said underside being sealed off from the environment by the circumferential sealing element. By virtue of the configuration in this embodiment according to the invention, the places that are usually difficult to clean, for example screw holes, are therefore already arranged to be inaccessible from outside.

According to the invention, the clamping of the sealing element on the handle housing is achieved by the fact that, circumferentially around each trough-shaped depression for receiving a switch element, a groove is formed in the handle housing in order to receive the respective sealing element, wherein, with the sealing element inserted, the respective groove can be covered by a clamping plate that is fastenable to the handle housing. The clamping plate for its part is advantageously fastenable to the handle housing via a latch connection.

According to a preferred embodiment for forming a handle according to the invention, it is proposed that the handle housing is triangular in cross section, and that a trough-shaped depression, in which a switch element is mounted so as to be pressed resiliently into the handle housing, is formed in each of the three side faces of the handle housing. When the handle is used on a medical holding arm, the handle serves to release the hinges of the holding arm via the switch elements when the holding arm is to be repositioned. At the moment when the operator actuates the switch elements and releases the hinges of the holding arm, the operator has to take up the full weight of the holding arm via the purchase on the handle. The triangular shape of the handle housing affords a firm hold and also prevents twisting of the handle in the operator's hand, as can happen when using handles with a round shape.

It is further proposed by the invention that at least one electrical contact, for example a button, is arranged underneath each switch element, such that the switch element activates the associated at least one electrical contact when pressed into the handle housing. The at least one electrical contact is advantageously arranged in the trough-shaped depression of the handle housing.

According to a practical embodiment of the invention, it is proposed that two electrical contacts spaced apart from each other are arranged underneath each switch element, wherein the two electrical contacts of each switch element are connected in parallel. The use of two electrical contacts also permits a tilting actuation of the switch element via the spring element. By virtue of the parallel connection of the two electrical contacts, it is immaterial, for generation of a switching signal, whether the front or the rear electrical contact is activated.

The invention further relates to a method for actuating the switch elements of an autoclavable handle, wherein at least two switch elements that can be pressed resiliently into the handle housing are mounted in the handle housing. In order to increase the operational reliability of the handle and in particular to exclude accidental actuation of a switch element, the invention proposes that all of the switch elements arranged in the handle housing have to be actuated simultaneously to generate a switching signal. Therefore, accidental actuation of just some of the switch elements of the respective handle remains harmless.

To generate a switching signal only when all of the switch elements are actuated simultaneously, it is proposed according to the invention that all of the switch elements arranged in the handle housing are connected in series.

To monitor the individual switch elements in relation to a short-circuit defect, it is proposed according to the invention that each switch element is monitored by means of a safety circuit operating according to the quiescent current principle.

Finally, the invention proposes that all of the switch elements of a handle are monitored, by means of a timer, for the presence of a short-circuit defect, in such a way that, if a switch element fails, all of the other switch elements of this handle are deactivated. In use on a medical holding arm, when the switch elements are deactivated, all of the hinges of the holding arm are held in the position blocking the hinges.

Further features and advantages of the invention will become clear from the appended drawings in which an illustrative embodiment of an autoclavable handle according to the invention is depicted only by way of example, without limiting the invention to this illustrative embodiment.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
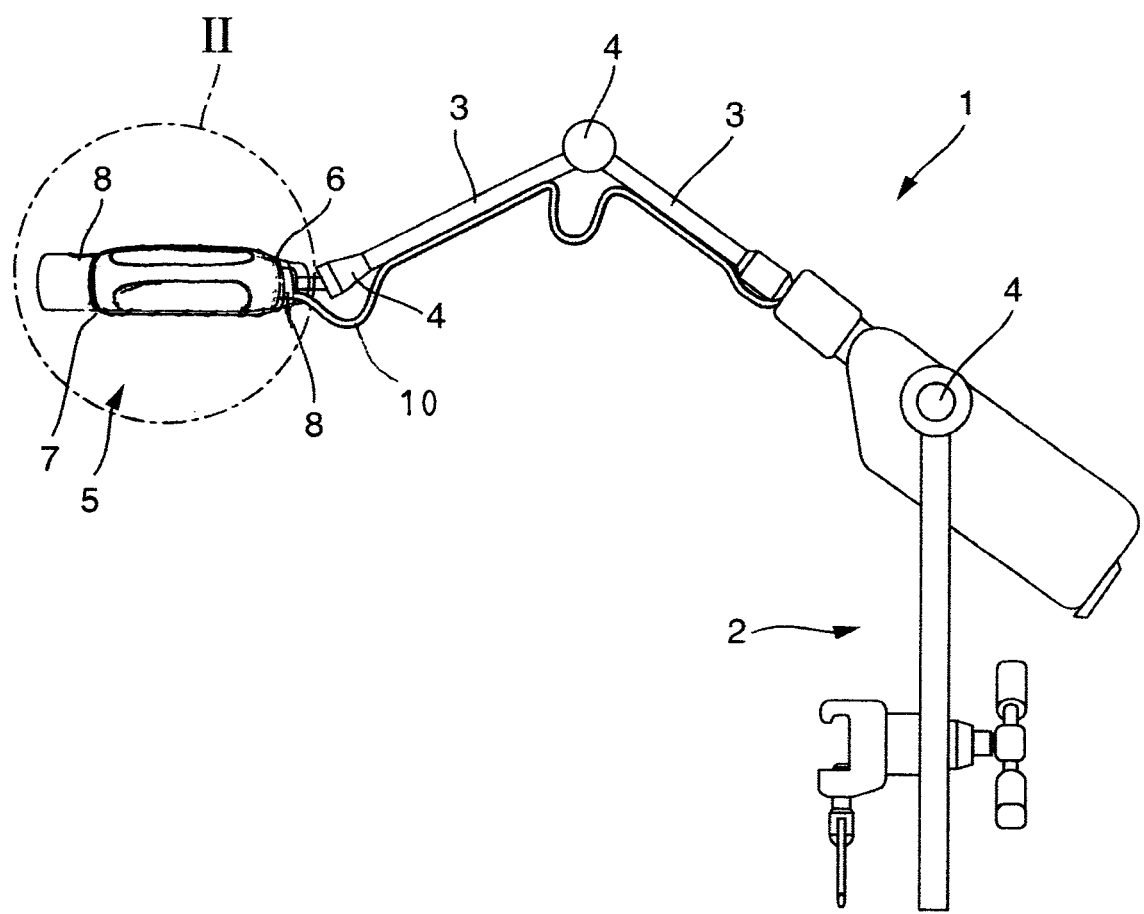
FIG. 1 is a schematic view of a medical support arm.

Referring to the drawings, FIG. 1 is a schematic view of a medical holding arm 1 composed of a base part 2 and of a plurality of arm segments 3 that are connected to each other and to the base part 2 via hinges 4. During operations, holding arms 1 of this kind serve to hold instruments, or objects in general at the operating site, in most cases above the patient, in order thereby to aid the operating surgeon. Otherwise, the operating surgeon or an assistant would themselves have to hold the instruments in the intended position relative to the patient.

To change the holding position of the holding arm 1, one or more hinges 4 of the holding arm 1 have to be released and, after the holding arm 1 has been repositioned, they have to be blocked again in order to fix the holding arm 1 in the new position. The release of the holding system of the holding arm 1 and the renewed blocking are effected by way of a handle 5 in which various electrical and/or electro-mechanical switch elements are arranged, such as buttons in particular.

Since the holding arms 1 are arranged in the sterile region of the operating theater but are not autoclavable as a whole, at least the non-dismantlable base part 2 of the holding arm 1 is covered beneath sterile drapes and hoods during the operation. Only the autoclavable regions, for example the handles 5 themselves, remain freely accessible and, unless they are designed as disposable articles, they have to be sterilized after each use. The customary form of sterilization is by autoclaving in an autoclave.

To ensure that the person operating the handle 5 can take up the load of the support arm 1 directly when unblocking the hinges 4, the handle 5 for operating the support arm 1 is advantageously coupled to the support arm 1, as shown in FIG. 1, such that it is fixedly connected to the support arm 1 during the operation but is releasable from the support arm 1 in order to permit autoclaving.

In the holding arm 1 shown in FIG. 1, the handle 5 is arranged such that, seen in the longitudinal direction of the handle 5, it is coupled with its proximal end 6 to the support arm 1, and a medical instrument to be positioned relative to the patient can be fastened to the distal end 7 of the handle 5 as seen in the longitudinal direction of the handle 5.

The connection of the handle 5 to the support arm 1, or to a medical instrument to be attached, is effected via coupling attachments 8, which are formed at the proximal end 6 and distal end 7 of a handle housing 9 of the handle 5. These coupling attachments 8 are structural parts which are formed integrally onto the handle housing 9 from the outside and which have no connection to the interior of the handle housing 9 and thus also have no seam or join to the region of the handle housing 9.

Figure 2:
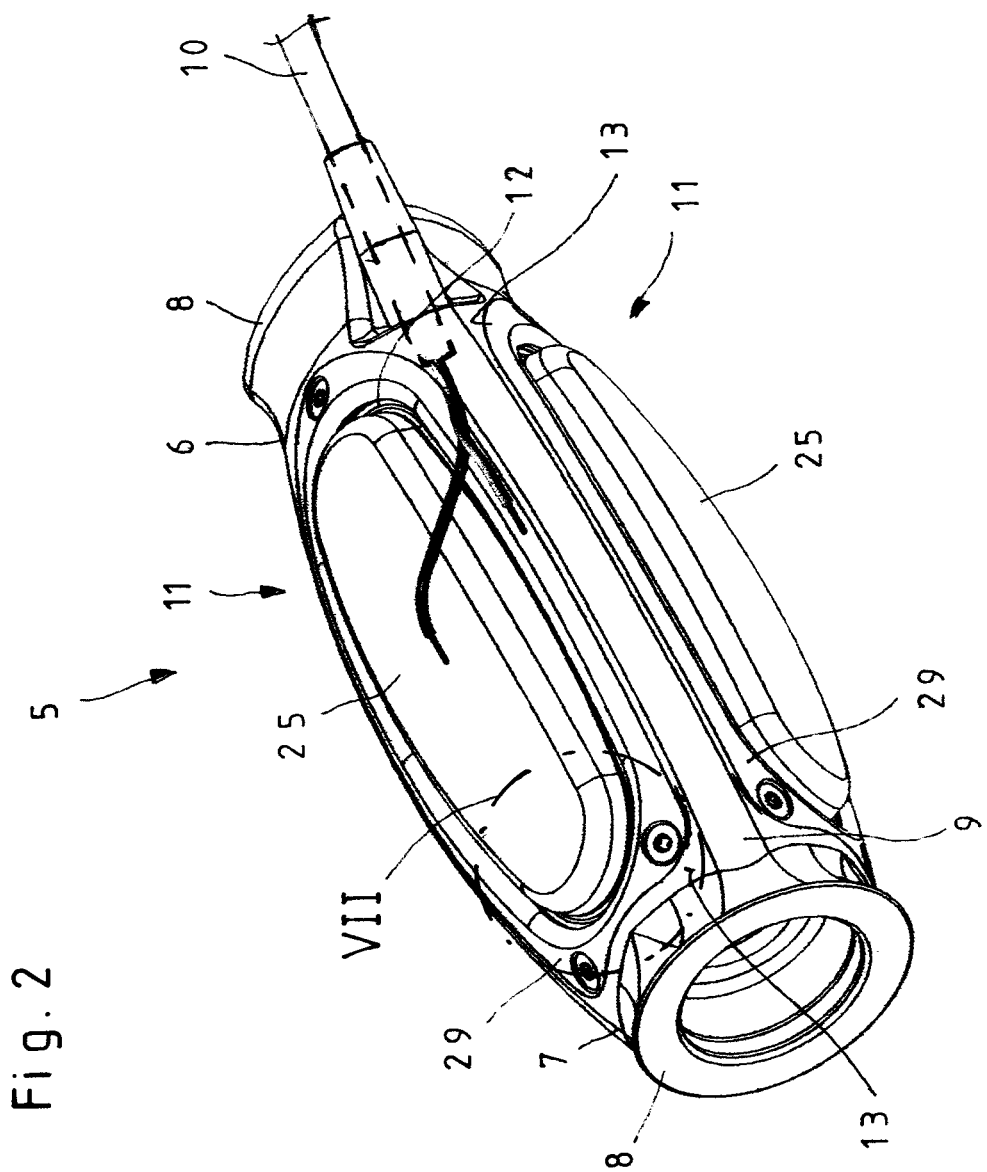
FIG. 2 is an enlarged perspective view of the detail II according to FIG. 1, depicting an autoclavable handle according to the invention.

In the embodiment shown in FIGS. 1 and 2, the handle 5 is provided with an electrical cable 10 for energy supply and for transmission of the switching signals. Alternatively, however, it is also possible for the handle 5 to be configured without cables, in which case the switching signals are then transmitted from the handle 5 to the support arm 1 as radio signals, and the handle 5 has a dedicated energy supply in the form of a battery or an accumulator.

The construction of the handle 5 is explained in detail below with reference to FIGS. 2 to 12.

The handle 5 is composed principally of a handle housing 9 in which a plurality of switch elements 11 are mounted in such a way that the switch elements 11 can be pressed resiliently into the handle housing 9. To ensure that the switch elements 11, mounted movably in the handle housing 9 relative to the rigid handle housing 9, can be sealed off from the handle housing 9 in order thereby to permit the autoclaving of the handle 5, each switch element 11 has a circumferential sealing element 12, which is made of an autoclavable material, for example silicone, and which is fastened on the one hand to the handle housing 9 and on the other hand to the switch element 11.

Figure 3:
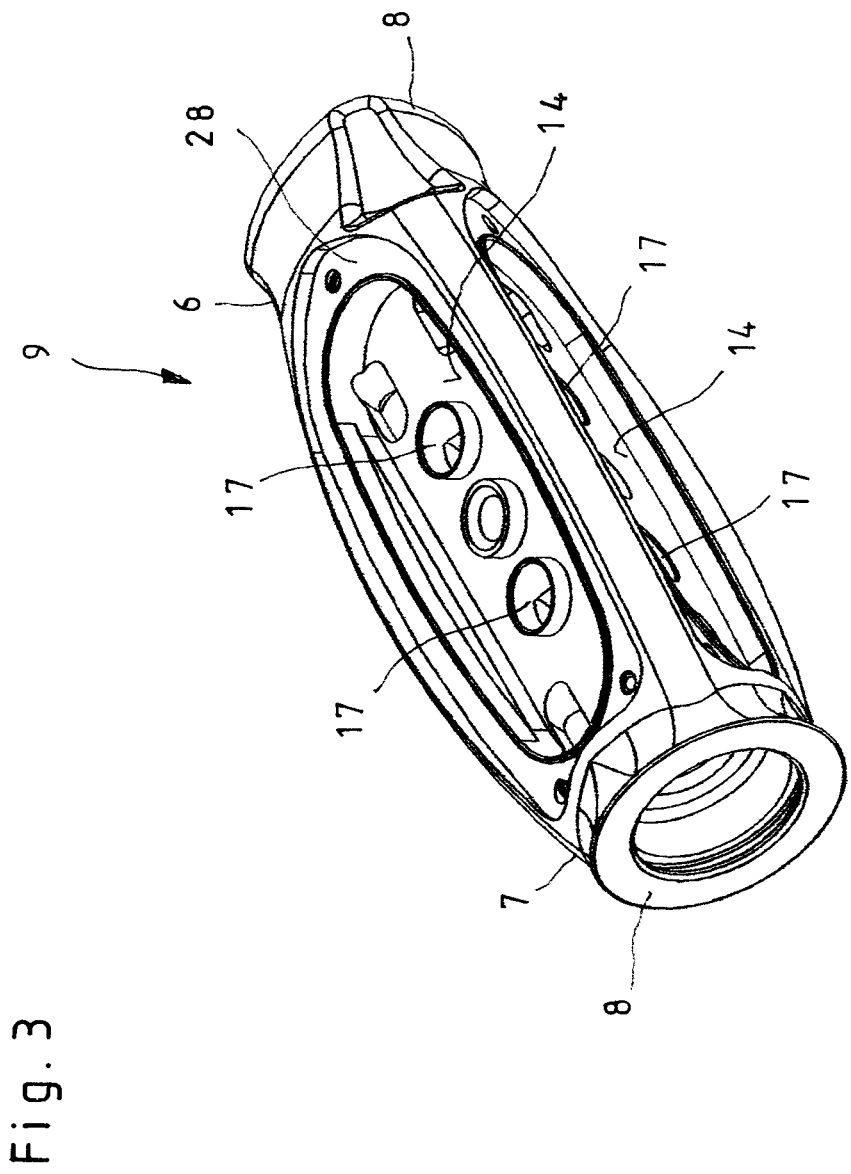
FIG. 3 is a perspective view of the handle housing of the handle according to FIG. 2.
Figure 4:
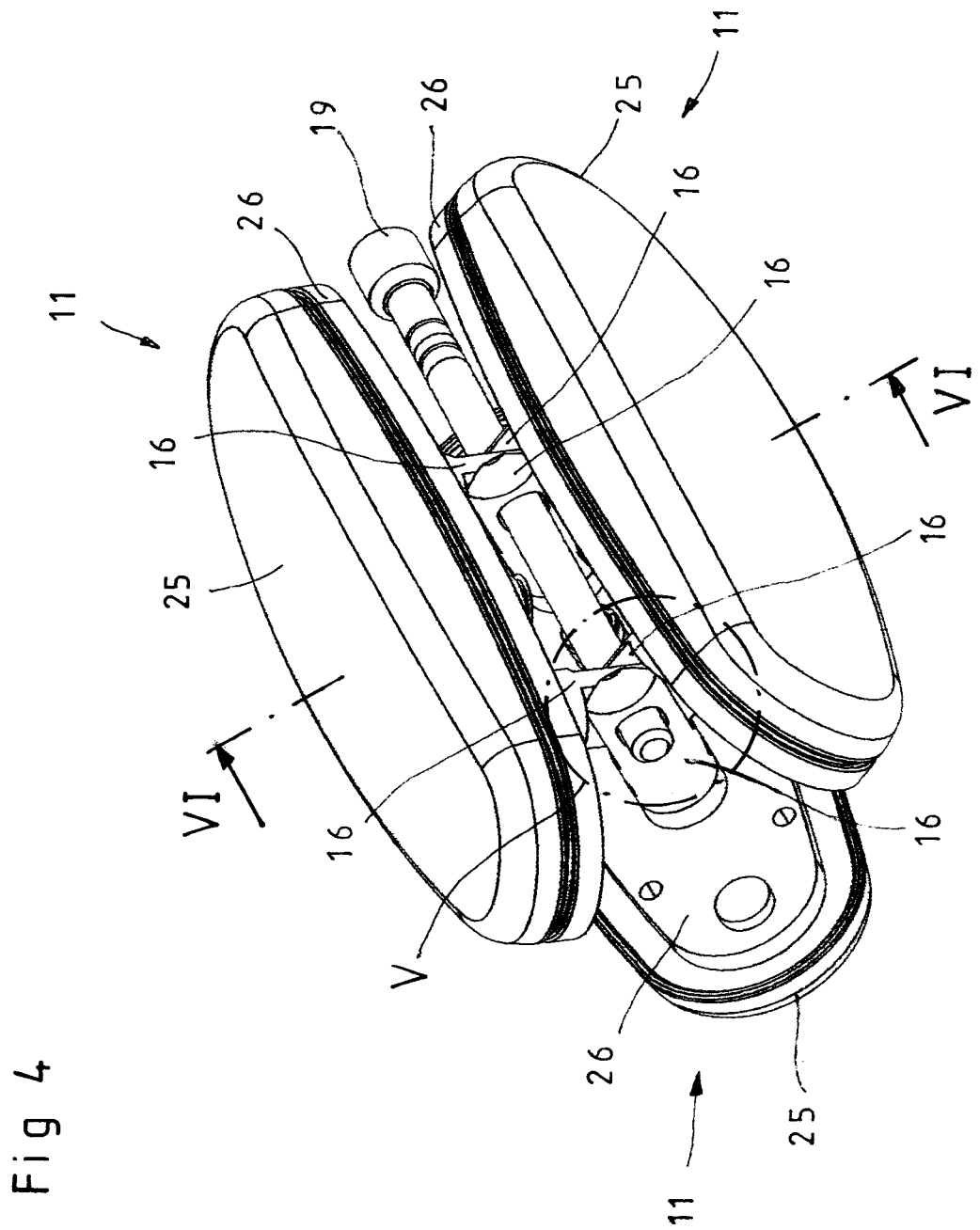
FIG. 4 is a perspective view according to FIG. 2, but depicts the handle without the handle housing.

As will be seen from the illustrative embodiment in FIGS. 2 to 4, the handle housing 9 of the handle 5 is triangular in cross section, and a switch element 11 is arranged in each one of the three side faces 13 of the handle housing 9.

When the handle 5 is used on a medical holding arm 1, the handle 5 serves to release the hinges 4 of the holding arm 1 via the switch elements 11 when the holding arm 1 is to be repositioned. At the moment when the operator actuates the switch elements 11 and releases the hinges 4 of the holding arm 1, the operator has to take up the full weight of the holding arm 1 via the purchase on the handle 5. By way of the edges of the triangular shape of the handle housing 9, and the edges of the switch elements 11 protruding beyond the side faces 13 of the handle housing 9, the handle 5 affords a firm hold and also prevents twisting of the handle 5 in the operator's hand, as can otherwise happen when using handles 5 with a round shape.

The switch elements 11 are arranged in trough-shaped depressions 14 of the handle housing 9 and are mounted in the handle housing 9 via webs 16 arranged on the underside 15 of the respective switch element 11, for which purpose openings 17 for passage of the webs 16 are formed in the trough-shaped depression 14.

In the illustrative embodiment shown, each switch element 11 is mounted in the handle housing 9 via in each case two spaced apart webs 16, although it is of course also possible to provide only one web 16 or, for example, also three webs 16.

For mounting the switch elements 11 in the handle housing 9, an oblong hole 18 is formed in each web 16, running in the longitudinal direction of the respective web 16, and serves to receive a common axle 19 passing through the oblong holes 18 of all the webs 16. In the assembled state of the handle 5, the axle 19 is in a fixed position in the handle housing 9. The mounting of the webs 16 on the axle 19 can be seen in particular from FIG. 4.

Figure 5:
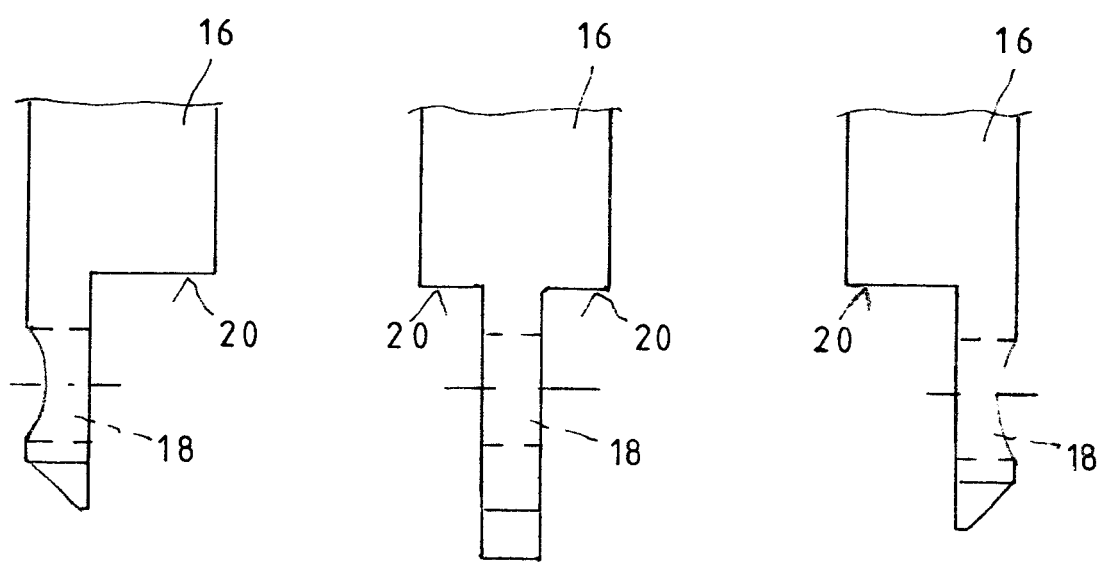
FIG. 5 is an enlarged view of the detail V according to FIG. 4.
Figure 6:
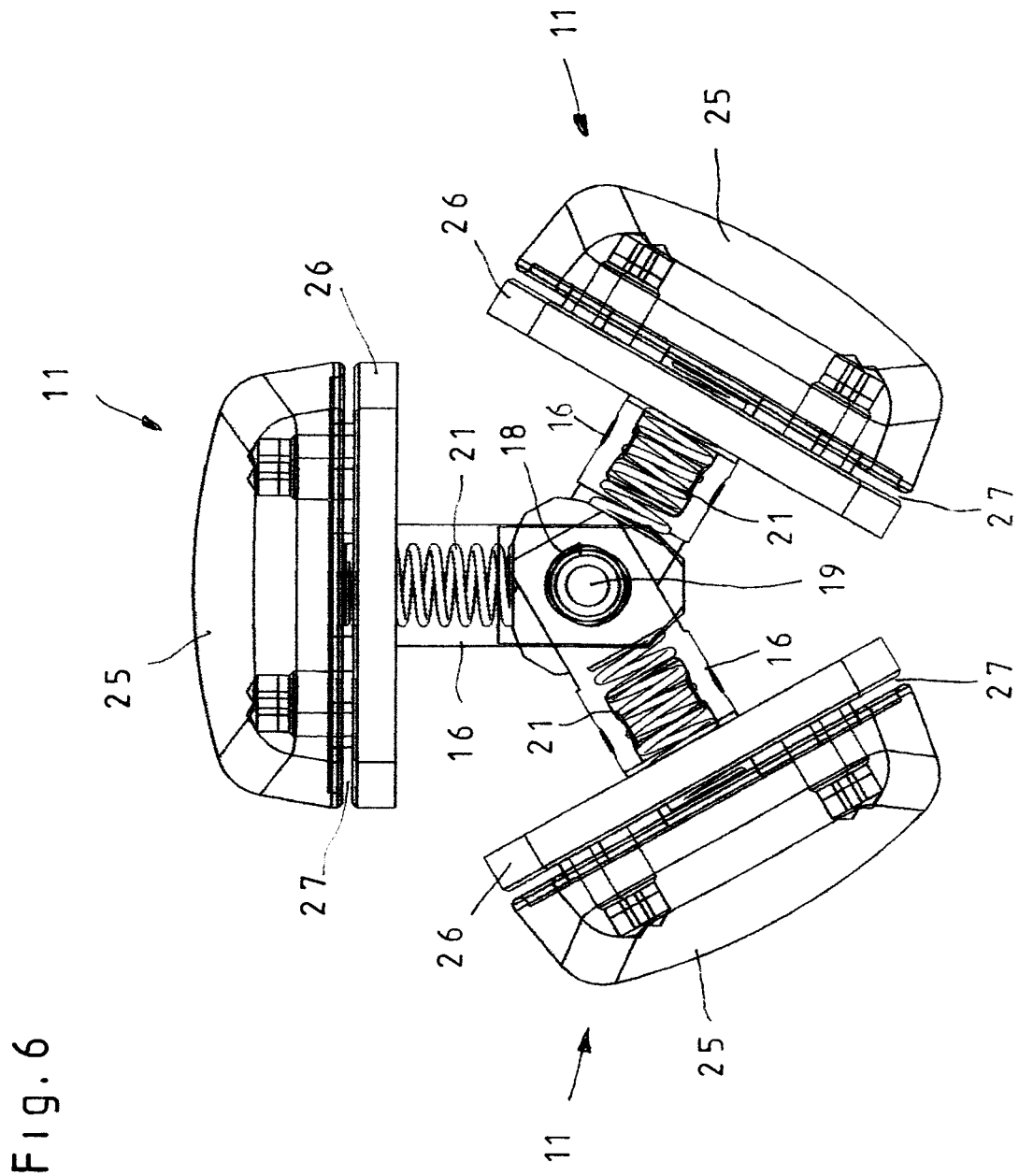
FIG. 6 is a section along the line VI-VI according to FIG. 4.

To allow the front and rear webs 16, respectively, of the three switch elements to be mounted as closely as possible next to each other on the common axle 19, the webs 16 have milled recesses 20 in the region of the oblong holes 18, as can be seen from FIG. 5.

The switch elements 11 are each pressed resiliently into the handle housing 9 by a respective spring element 21, which bears with one end on the underside 15 of the respective switch element 11 and is supported with the other end on the bottom of the trough-shaped depression 14 of the handle housing 9. Advantageously, the spring element 21 is arranged centrally between the two webs 16 of the respective switch element 11, such that it is not just possible for the switch element 11 to be pressed vertically downward as a whole but also to be actuated so as to tilt forward or rearward.

By means of the spring elements 21 supported on the bottom plate of the trough-shaped depressions 14, the switch elements 11 are pressed outward until they bear, with the lower edges of the oblong holes 18 formed in the webs 16, on the common axle 19. The switch elements 11 thus have a work stroke corresponding to the length of the oblong holes 18 formed in the webs 16. This described type of mounting of the switch elements 11 on the common axle 19 on the one hand ensures a secure and captive bearing of the switch elements 11 in the handle housing 9 and on the other hand guarantees at the same time a defined work stroke for the switch elements 11 that can be pressed into the handle housing 9.

In order to generate a switching signal, at least one electrical contact 22, for example a button, is arranged underneath each switch element 11, such that the switch element 11 activates the associated at least one electrical contact 22 when pressed into the handle housing 9. This at least one electrical contact 22 is arranged in the trough-shaped depression 14 of the handle housing 9 underneath the respective switch element 11, as is shown in FIG. 7.

Advantageously, two electrical contacts 22 spaced apart from each other are arranged underneath each switch element 11, in which case the two electrical contacts 22 of each switch element 11 are connected in parallel. The use of two electrical contacts also permits a tilting actuation of the switch element 11 via the spring element 21. By virtue of the parallel connection of the two electrical contacts 22, it is immaterial, for generation of a switching signal, whether the front and rear electrical contacts 22 are activated separately or simultaneously.

Figure 7:
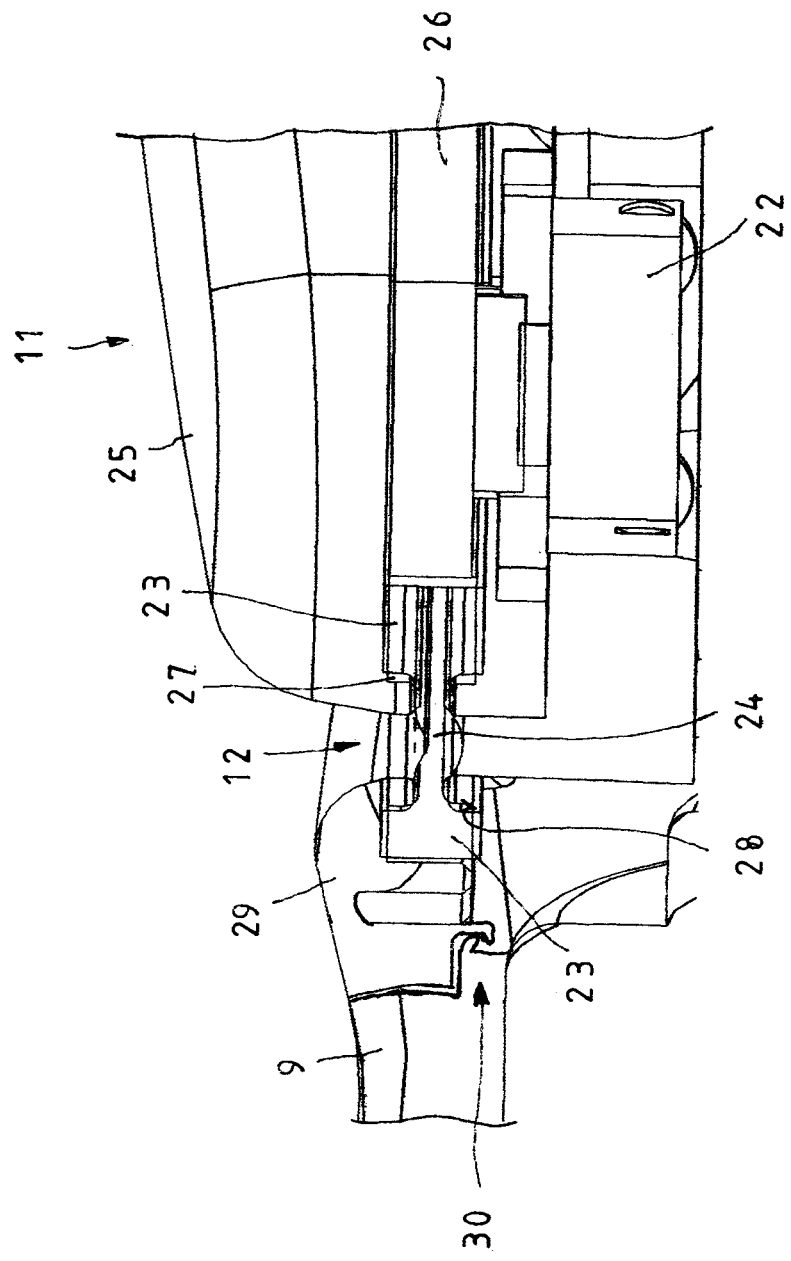
FIG. 7 is a longitudinal section through the detail VII according to FIG. 2.

The reliable seal between the handle housing 9, on the one hand, and the switch element 11 that can be pressed in, on the other hand, is provided via the circumferential sealing element 12 surrounding each switch element 11, wherein the sealing element 12 is mounted with clamping engagement both on the handle housing 9 and on the respective switch element 11, as can be seen from the sectional drawing according to FIG. 7. With the sealing element 12 mounted with clamping engagement on both sides, a secure and positionally fixed hold of the sealing element 12 is guaranteed even upon actuation of the associated switch element 11.

Figure 10:
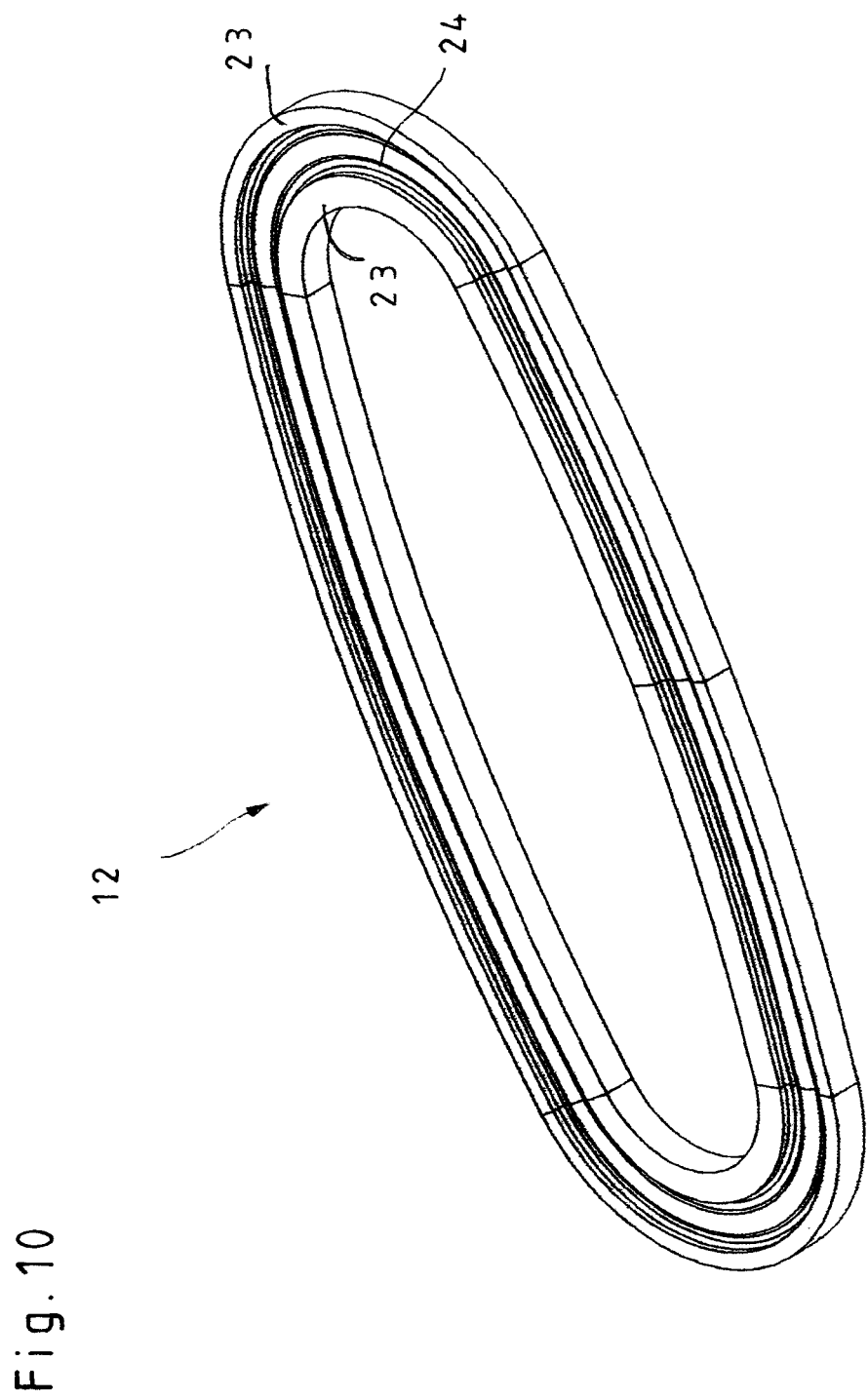
FIG. 10 is an enlarged perspective view of a sealing element of the handle according to FIG. 2.

As will be seen from FIGS. 7 and 10, each sealing element 12 has two bead-shaped clamping regions 23 which are spaced radially apart from each other and are connected to each other via an elastic connecting web 24. The elastic connecting web 24 ensures that the switch elements 11 are pressed resiliently into the handle housing 9 and also that the sealing element 12 is mounted on the handle housing 9 and on the switch element 11 with clamping engagement.

Figure 8:
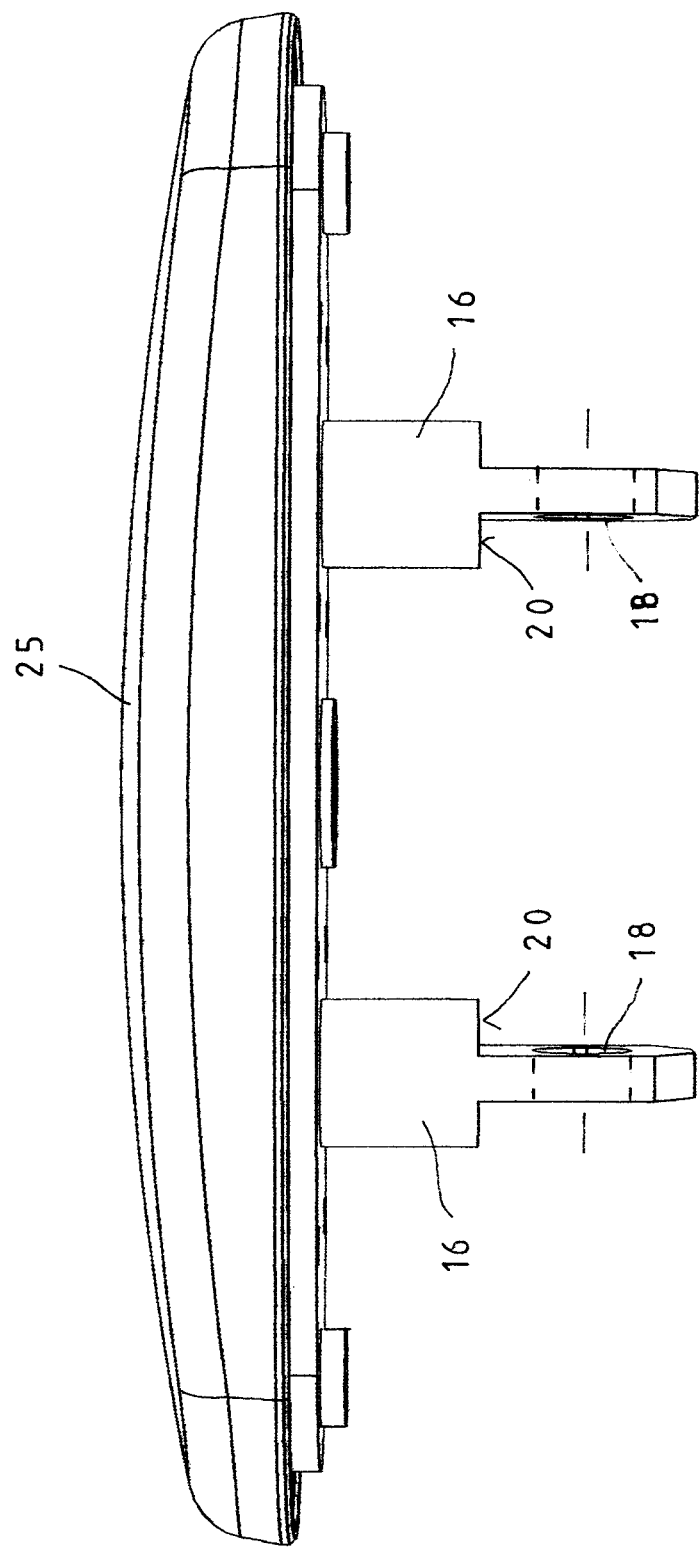
FIG. 8 is an enlarged side view of the grip plate of a switch element of the handle according to FIG. 2.
Figure 9:
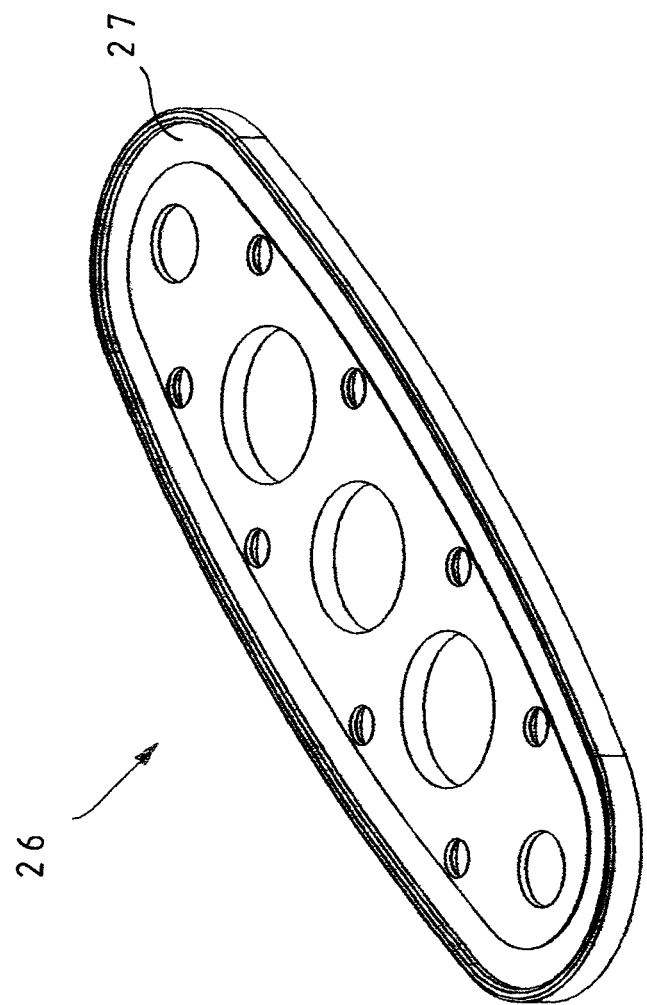
FIG. 9 is an enlarged perspective view of the screw plate of a switch element of the handle according to FIG. 2.

As will be seen by comparing FIGS. 7, 8 and 9, each switch element 11 is composed of an upper grip plate 25 and a lower screw plate 26, wherein the circumferential sealing element 12 is held clamped in a sealing seat 27 between the grip plate 25 and the screw plate 26. The use of the two part structure of the switch elements 11 with the lower screw plate 26 has the advantage that the sealing element 12 can be easily secured with clamping engagement on the respective switch element 11 and all of the necessary screw connections are arranged on the underside of the switch element 11, said underside being sealed off from the environment by the circumferential sealing element 12. By virtue of the configuration in this embodiment, the places that are usually difficult to clean, for example screw holes, are therefore already arranged to be inaccessible from outside.

Figure 11:
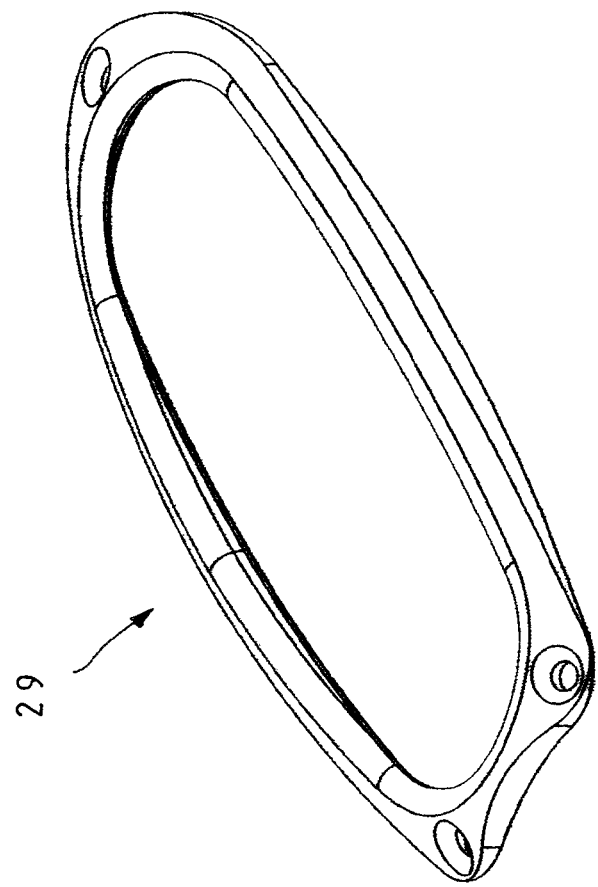
FIG. 11 is an enlarged perspective view of a clamping plate of the handle according to FIG. 2.

The sealing element 12 is clamped securely on sides of the handle housing 9 by virtue of the fact that, circumferentially around each trough-shaped depression 14 for receiving a switch element 11, a groove 28 is formed in the handle housing 9 in order to receive the respective sealing element 12, wherein, with the sealing element 12 inserted, the respective groove 28 can be covered by a clamping plate 29 that is fastenable to the handle housing 9, according to FIG. 11. The clamping plate 29 for its part can be fastened to the handle housing 9 via a latch connection 30.

Through the use of the switch element 11 which can be pressed resiliently into the handle housing 9, with the circumferential sealing element 12 made of an autoclavable material that sealingly bridges the gap between the movable switch element 11 and the rigid handle housing 9, a handle 5 is made available which, while being simple and safe to use, does not require any joins in the handle housing 9 and therefore ensures reliable cleaning in the autoclave.

To increase the operational safety of the handle 5, and in particular to exclude accidental actuation of a switch element 11, all of the switch elements 11 arranged in the handle housing 9 have to be actuated simultaneously in order to generate a switching signal. For this purpose, all of the switch elements 11 arranged in the handle housing 9 are connected in series. Therefore, accidental actuation of only individual switch elements 11 of the respective handle 5 remains harmless.

The procedure by which a handle 5 of the above-described configuration is actuated is explained briefly below.

In the illustrative embodiment in question, two electrical contacts 22 are located under each switch element 11, i.e. one at each end of the respective switch element 11 as seen in the longitudinal direction of the handle housing 9. These two electrical contacts 22 of the switch element 11 are connected in parallel and thus act electrically like one common contact 22 but, because of their spatial separation, they also react when the switch element 11, on account of the resilient mounting on the spring element 21, is actuated to tilt only forward or only rearward.

The electrical contacts 22 of the various switch elements 11 of a handle 5 are electrically connected in series, such that a switching signal can only be generated if all of the switch elements 11 are actuated simultaneously.

In order to be able to distinguish this switching state from short circuits on the feed line, resistors 31 that can be evaluated according to the quiescent current principle are connected in parallel and in series to the electrical contacts 22.

The short circuit of an individual electrical contact 22 can be detected by the parallel resistor being replaced by three resistors 31 each of a third of the value, and these three resistors 31 are each connected in parallel to only one electrical contact 22. Thus, an electronic evaluation unit can detect whether no switch element or one, two or three switch elements 11 is/are pressed.

Figure 12:
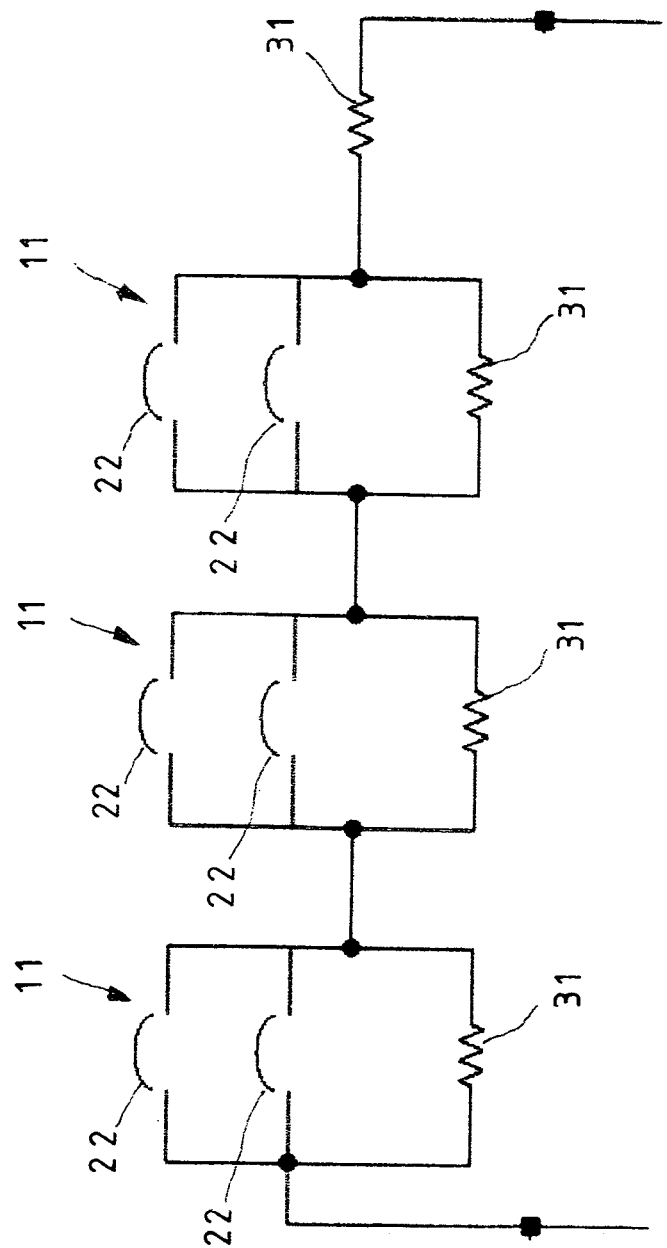
FIG. 12 is a schematic block diagram of the switch elements of the handle.

FIG. 12 shows a schematic block diagram of the above-described circuitry of the switch elements 11 of the handle 5.

If an electrical contact 22 has a short-circuit defect, is active for longer, without the other switch elements 11 being pressed, a timer can detect this and transfer the entire system to a secure state. In use on a medical holding arm 1, when the switch elements 11 are deactivated, all of the hinges 4 of the holding arm 1 are held in the position blocking the hinges In addition to the above-described handle 5 being able to be autoclaved, this handle 5 is distinguished by being simple and safe for the operator to use.

While specific embodiments of the invention have been shown and described in detail to illustrate the application of the principles of the invention, it will be understood that the invention may be embodied otherwise without departing from such principles.

What is claimed is:

1. An autoclavable handle comprising:
   a handle housing;
   at least one switch element mounted to the handle housing;
   at least one web arranged on an underside of the at least one switch element, wherein the at least one switch element is mounted to the handle housing via the at least one web with the at least one switch element being resiliently pressable relative to the handle housing;
   a circumferential sealing element wherein the at least one switch element is sealed off from the handle housing via the circumferential sealing element;
   an axle connected to the handle housing; and
   a spring element mounted on the switch element, wherein:
   an oblong hole is formed in the at least one web and runs in a longitudinal direction of the web and the web is mounted in the handle housing via the axle passing through the oblong hole; and
   the spring element is mounted on the switch element in such a way that the spring element presses the switch element outward from the handle housing, such that a working path of the switch element is defined by a length of the oblong hole.

2. The autoclavable handle as claimed in claim 1, wherein:
   the at least one switch element is arranged in a trough-shaped depression of the handle housing;
   an opening, for passage of the at least one web, is formed in the depression; and
   the spring element bears with one end on an underside of the switch element and is supported with another end on a bottom of the trough-shaped depression of the handle housing.

3. The autoclavable handle as claimed in claim 1, further comprising another web arranged on the underside of the at least one switch element and with an oblong hole formed in the other web extending in a longitudinal direction of the other web to provide two webs spaced apart from each other, wherein:
   the at least one switch element is mounted in the handle housing via the two webs spaced apart from each other;
   the at least one switch element is arranged in a trough-shaped depression of the handle housing;
   a separate opening is formed in the trough-shaped depression for each web; and
   the webs spaced apart from each other are mounted in the handle housing on the axle as a common axle.

4. The autoclavable handle as claimed in claim 1, further comprising:
   another switch element to provide a plurality of switch elements; and
   at least one web arranged on an underside of the other switch element, wherein:
   each of the plurality of switch elements is mounted in an associated trough-shaped depression of the handle housing;
   a separate opening is formed in each trough-shaped depression for each web; and
   the webs of all of the switch elements are mounted on the axle as a common axle in the handle housing.

5. The autoclavable handle as claimed in claim 4, further comprising another circumferential sealing element to provide a plurality of sealing elements, the other switch element being sealed off from the handle housing via the other circumferential sealing element, each of the plurality of sealing elements mounted with a clamping engagement both on the handle housing and on the respective switch element.

6. The autoclavable handle as claimed in claim 5, wherein each sealing element comprises two bead-shaped clamping regions which are spaced radially apart from each other and are connected to each other via an elastic connecting web.

7. The autoclavable handle as claimed in claim 5, wherein:
   each switch element is comprised of an upper grip plate and a lower screw plate;
   the circumferential sealing element is secured with clamping engagement in a sealing seat between the grip plate and the screw plate.

8. The autoclavable handle as claimed in claim 5, further comprising a clamping plate wherein, circumferentially around each trough-shaped depression for receiving a switch element, a groove is formed in the handle housing in order to receive the respective sealing element, wherein, with the respective sealing element received, the respective groove is covered by the clamping plate and the clamping plate is fastened to the handle housing.

9. The autoclavable handle as claimed in claim 8, further comprising a latch connection wherein the clamping plate is fastened to the handle housing via the latch connection.

10. The autoclavable handle as claimed in claim 1, further comprising at least two other switch elements to provide at least three switch elements, wherein:
    the handle housing is triangular in cross section; and
    a trough-shaped depression is formed in each of the three side faces of the handle housing; and
    one of the three switch elements is arranged in each trough-shaped depression so as to be pressed resiliently into the handle housing.

11. The autoclavable handle as claimed in claim 1, further comprising at least one electrical contact, wherein:

the at least one electrical contact is arranged underneath the at least one switch element, such that the at least one switch element activates the at least one electrical contact when pressed into the handle housing.

12. The autoclavable handle as claimed in claim 11, wherein:
the at least one switch element is arranged in a trough-shaped depression of the handle housing; and
the at least one electrical contact is arranged in the trough-shaped depression of the handle housing.

13. The autoclavable handle as claimed in claim 11, further comprising two electrical contacts arranged underneath the at least one switch element wherein the two electrical contacts are connected in parallel.

14. The autoclavable handle comprising:
a handle housing;
a plurality of switch elements mounted to the handle housing, wherein: the switch elements are respectively arranged in trough-shaped depressions of the handle housing;
a common axle in the handle housing;
webs, wherein each of the webs is arranged on an underside of a respective one of the switch elements, wherein a separate opening is formed in each of the trough-shaped depressions for passage of each of the webs, each of the switch elements is mounted to the handle housing via the respective one of the webs with the switch elements being resiliently pressable relative to the handle housing, and the webs of all of the switch elements are mounted on the common axle in the handle housing; and
circumferential sealing elements, wherein each of the switch elements is sealed off from the handle housing via a respective one of the circumferential sealing elements.

15. The autoclavable handle as claimed in claim 14, further comprising:
a spring element mounted on the switch elements, wherein:
an oblong hole is formed in the webs and runs in a longitudinal direction of the webs and the webs are mounted in the handle housing via the common axle passing through the oblong hole; and
the spring element is mounted on the switch elements in such a way that the spring element presses the respective switch element outward from the handle housing, such that a working path of the switch elements is defined by a length of the oblong hole.

16. The autoclavable handle as claimed in claim 14, wherein:
an oblong hole is formed in each of the webs and runs in a longitudinal direction of the webs and the webs are mounted in the handle housing via the common axle passing through the oblong hole; and
the switch elements are resiliently pressable relative to the handle housing such that a working path of the switch elements is defined by a length of the oblong hole.

17. A method for actuating autoclavable handle, the method comprising the steps of:
providing autoclavable handle comprising a handle housing, a plurality of switch elements mounted to the handle housing, wherein the switch elements are respectively arranged in trough-shaped depressions of the handle housing, a common axle in the handle housing, webs, wherein each of the webs is arranged on an underside of a respective one of the switch elements, wherein a separate opening is formed in each of the trough-shaped depressions for passage of each of the webs, wherein each of the switch elements is mounted to he handle housing via the respective one of the webs with the switch elements being resiliently pressable relative to the handle housing, and the webs of all of the switch elements are mounted on the common axle in the handle housing and circumferential sealing elements wherein each of the switch elements is sealed off from the handle housing via a respective one of the circumferential sealing elements; and
pressing the at least one switch element relative to the handle housing.

18. The method as claimed in claim 17, wherein:
each of the plurality of switch elements connected to the handle housing are actuated simultaneously to generate a switching signal.

19. The method as claimed in claim 17, wherein:
all of the switch elements connected to the handle housing are connected in series.

20. The method as claimed in claim 17, wherein:
an oblong hole is formed in each of the webs and runs in a longitudinal direction of the webs and the webs are mounted in the handle housing via the common axle passing through the oblong hole; and
the switch elements are resiliently pressable relative to the handle housing such that a working path of the switch elements is defined by a length of the oblong hole.

* * * * *